US006521775B2

(12) United States Patent
Cheruvallath et al.

(10) Patent No.: US 6,521,775 B2
(45) Date of Patent: Feb. 18, 2003

(54) PROCESS FOR THE SYNTHESIS OF OLIGOMERIC COMPOUNDS

(75) Inventors: Zacharia S. Cheruvallath, San Diego, CA (US); Vasulinga T. Ravikumar, Carlsbad, CA (US); Douglas L. Cole, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/016,465

(22) Filed: Dec. 11, 2001

(65) Prior Publication Data

US 2002/0055623 A1 May 9, 2002

Related U.S. Application Data

(60) Division of application No. 09/349,659, filed on Jul. 8, 1999, which is a continuation-in-part of application No. 09/111,678, filed on Jul. 8, 1998, now Pat. No. 6,326,478.

(51) Int. Cl.$^7$ .............................. C07F 9/02; C07H 21/00

(52) U.S. Cl. .................. 558/70; 536/23.1; 536/24.3; 536/24.5; 536/25.34; 435/91.2

(58) Field of Search ............................. 536/23.1, 24.3, 536/24.5, 25.34; 558/70; 436/91.2

(56) References Cited

U.S. PATENT DOCUMENTS

| | | | |
|---|---|---|---|
| 3,687,808 A | 8/1972 | Merigan et al. | |
| 4,415,732 A | 11/1983 | Caruthers et al. | |
| 4,458,066 A | 7/1984 | Caruthers et al. | |
| 4,500,707 A | 2/1985 | Caruthers et al. | |
| 4,668,777 A | 5/1987 | Caruthers et al. | |
| 4,725,677 A | 2/1988 | Köster et al. | |
| 4,816,571 A | 3/1989 | Andrus et al. | |
| 4,973,679 A | 11/1990 | Caruthers et al. | |
| 5,026,838 A | 6/1991 | Nojiri et al. | |
| 5,132,418 A | 7/1992 | Caruthers et al. | |
| RE34,069 E | 9/1992 | Köster et al. | |
| 5,210,264 A | 5/1993 | Yau ............................ | 558/167 |
| 5,212,295 A | 5/1993 | Cook ......................... | 536/26.7 |
| 5,670,633 A | 9/1997 | Cook et al. ................. | 536/23.1 |
| 6,127,533 A | 10/2000 | Cook et al. ................. | 536/23.6 |
| 6,166,197 A | 12/2000 | Cook et al. ................. | 536/24.5 |
| 6,172,209 B1 | 1/2001 | Manoharan et al. ........ | 536/26.7 |
| 6,271,358 B1 | 8/2001 | Manoharan et al. ........ | 536/23.1 |
| 6,326,478 B1 * | 12/2001 | Cheruvallath et al. ..... | 536/23.1 |
| 6,399,756 B1 * | 6/2002 | Cheruvallath et al. ..... | 536/25.3 |

FOREIGN PATENT DOCUMENTS

EP 0 506 242 A1 3/1992

OTHER PUBLICATIONS

Grzeszczyk et al., "The Synthesis of Two Repeating Units of *Haemophilus influenzae* Type a Capsular Antigen," *Carbohydrate Research*, 175(2), 215–226 (Apr. 15, 1988).*

Fathi et al., "Synthesis of Properties of Combinatorial Libraries of Phosphoramidates," *Journal of Organic Chemistry*, 61(16), 5600–5609 (Aug. 9, 1996).*

Tabatadze et al., "Interaction of Short Oligonucleotide Derivatives with Nucleic Acids. III. Photomodification of DNA Targets Using Tandems of Short Oligonucleotide Derivatives," *Bioorg. Khim.*, 23(8), 642–647 (1997; Russian, English Abstr.).*

Sund et al., "Intra- and Intramolecuolar Nucleophilic Phosphorus—Sulfur Bond Cleavage. The Reaction of Fluoride Ion with O–Aryl–O,S–Dialkylphosporothioates, & Degradation of Phosphorothioate Linkage in di– Ribonucleotides by the Vicinal 2'–Hydroxyl Group," *Tetrahedron*, 45(23), 7523–7544 (1989).*

Watanabe et al., "Stepwise Degradation of Vicinal Diol and Sterically Hindered Alcohol Directed Toward D–Myo–Inositol 2,4,5–Trisphosphate," *Tetrahedron Letters*, 28(23), 2607–2610 (1987).*

Alul, R.H. et al., "Oxalyl–CPG: a labile support for synthesis of sensitive oligonucleotide derivatives", *Nucl. Acid Res.*, 1991, 19, 1527–1532 (Issue No. 7).

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Beigelman, L. et al., "Synthesis and biological activities of a phosphorodithioate analog of 2',5'–oligoadenylate", *Nucl. Acids Res.*, 1995, 23(19), 3989–3994.

Bielinska, A. et al., "Regulation of Gene Expression with Double–Stranded Phosphorothioate Oligonucleotides", *Science*, 1990, 250, 997–1000 (Nov. 16, 1990).

Brown, T. et al., "Modern machine–aided methods of oligodeoxyribonucleotide synthesis", *Oligonucleotides and Analogs A Practical Approach*, 1991, Chapter 1, Ekstein, F., ed., IRL Press, Oxford, 1–24.

Cook, P.D., "Medicinal chemistry of antisense oligonucleotides—Future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304 (Issue No. 3–4).

(List continued on next page.)

Primary Examiner—Samuel Barts
Assistant Examiner—Lawrence E Crane
(74) *Attorney, Agent, or Firm*—Woodcock Washburn LLP

(57) ABSTRACT

Synthetic processes are provided wherein oligomeric compounds are prepared having phosphodiester, phosphorothioate, phosphorodithioate, or other covalent linkages. Also provided are synthetic intermediates useful in such processes.

5 Claims, No Drawings

OTHER PUBLICATIONS

Efimov, V.A. et al., "New efficient sulfurizing reagents for the preparation of oligodeoxyribonucleotide phosphorothioate analogues", *Nucl. Acids Res.*, 1995, 23, 4029–4033 (Issue No. 20).

Englisch, U. et al., "Chemically Modified Oligonucleotides as Probes and Inhibitors", *Angew. Chem. Int. Ed. Eng.*, 1991, 30, 613–629 (Jun. 1991, Issue No. 6).

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699 (Issue No. 15).

Kamer, P.C.J. et al., "An Efficient Approach Toward the Synthesis of Phosphorothioate Diesters via the Schonberg Reaction", *Tetrahedron Letts.*, 1989, 30, 6757–6760 (Issue No. 48).

Kroschwitz, J.I. (ed.), "Polynucleotides", *Concise Encyclopedia of Polymer Science and Engineering*, 1990, John Wiley & Sons, New York, 858–859.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912 (Issue No. 25).

Miura, K. et al., "Blockwise Mechanical Synthesis of Oligonucleotides by the Phosphoramidite Method", *Chem Pharm. Bull.*, 1987, 35, 833–836.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Rao, M. V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842 (Issue No. 33).

Ravasio, N. et al., "Selective Hydrogenations Promoted by Copper Catalysts. 1. Chemoselectivity. Regioselectivity, and Stereoselectivity in the Hydrogenation of 3–Substituted Steroids", *J. Org. Chem.*, 1991, 56, 4329–4333 (Issue No. 13).

Sanghvi, Y.S., "Heterocyclic Base Modifications in Nucleic acids and their Applications in Antisense Oligonucleotides", *Antisense Research and Applications*, CRC Press, Boca Raton, 1993, Chapter 15, 273–288.

Secrist, J.A. et al., "Synthesis and Biological Activity of 4'–Thionucleosides", *10th International Rountable: Nucleosides, Nucleotides and their Biological Applications*, Sep. 16–20, 1992, Abstract 21, Park City, Utah, 40.

Stec, W.J. et al., "Stereospecific Synthesis of P–chiral Analogs of oligonucleotides", *Methods in Molecular Biology*, Humana Press, Totowa, NJ, vol. 20, 1993, Chapter 14, 285–313.

Stec, W.J. et al., "Novel route to oligo(deoxyribonucleoside phosphorothioates)", *Nucl. Acids Res.*, 1991, 19, 5883–5888 (Issue No. 21).

Stec, W.J. et al., "Bis (O,O–Diisopropoxy Phosphinothioyl) Disulfide—A Highly Efficient Sulfurizing Reagent for Cos-Effective Synthesis of Oligi(Nucleoside Phosphorothioate)s", *Tetrahedron Letts.*, 1993, 34, 5317–5320 (Issue No. 33).

Uznanski, B. et al., "Deoxyribonucleoside 3'–Phosphordiamidites as Substrates for Solid Supported Synthesis of Oligodeoxyribonucleotides and Their Phosphorothioate and DNA–Triester Analogues", *Tetra. Lett.*, 1987, 28(29), 3401–3404.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008 (Issue No. 26).

Wiesler, W. et al., "Synthesis of Phosphorodithioate DNA via Sulfur–Linked, Base–Labile Protecting Groups", *J. Org. Chem.*, 1996, 61, 4272–4281 (Issue No. 13).

Wolter, A. et al., Polymer Support Oligonucleotide Synthesis XX: Synthesis of a Henhectacosa Deoxynucleotide by use of a Dimeric Phosphoramidite *Nucleosides & Nucleotides*, 1986, 5, 65–77(Issue No. 1).

Wright, P. et al., "Large Scale Synthesis of Oligonucleotides via phosphoramidite Nucleosides and a High–loaded Polystyrene Support", *Tetrahedron Letts.*, 1993, 34, 3373–3376 (Issue No. 21).

Wu, H. et al., "Inhibition of in vitro transcription by specific double–stranded oligodeoxyribonucleotides", *Gene*, 1990, 89, 203–209.

Xu, Q. et al., "Efficient introduction of phosphorothioates into RNA oligonucleotides by 3–ethoxy–1,2, 4–dithiazoline–5–one (EDITH)", *Nucl. Acids Res.*, 1996, 24, 3643–3644 (Issue No. 18).

Xu, Q. et al., "Use of 1,2,4–diathiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24, 1602–1607 (Issue No. 9).

Basak, A. et al., "PPL–Catalysed Hydrolysis of 3,4–Disubstituted βLactams: Effect of Chain: Length and Stereochemisry on the Enantioselectivity," *Tetrahedron*, 1998, 54, 6529–6538.

Bianchi, D. et al., "Anhydrides as Acylating Agents in Lipase–Catalyzed Stereoselective Esterification of Racemic Alcohols," *J. Org. Chem.*, 1988, 53, 5531–5534.

Bisht, K. et al., "Biotransfromations in the Regioselective Deacetylation of Polyphenolic Peracetates in Organic Solvents," *Bioorg. Med. Chem.*, 1994, 2(10), 1015–1020.

Boland, W. et al., "Esterolytic and Lipolytic Enzymes in Organic Synthesis," *Synthesis*, 1991, 1049–1072 (Dec., 1991).

Chillemi, R. et al., "Chemoenzymatic Syntesis of Lysophophatidylnucleosides," *J. Org. Chem.*, 1998, 63, 3224–3229.

Lipshutz, B. et al., "Selective Deprotection of Alkyl vs. Arly Silyl Ethers," *Tetra. Lett.*, 1998, 39, 2495–2498.

Oriyama, T. et al., "Chemoselective and Practical Deprotection of Alkyl Trialkylsilyl Ethers in the Presence of Aryl Trialkylsilyl Ethers by a Catalytic Amount of Sc(OTf)$_3$," *Synlett*, 1998, 1047–1048 (Oct. 1998).

Parmar, V. et al., "Lipase–catalysed selective deacetylation of phenolic/enolic acetoxy groups in peracetylated benzyl phenyl ketones," *Bioorg. Med. Chem.*, 1998, 6, 109–118.

Parmar, V. et al., "Regioselective Enzyme–Catalyzed Deacetylation of Benzyl Phenyl Ketone Peracetates in Organic Solvents," *Bioorg. Med. Chem. Lett.*, 1993, 3(4), 585–588.

Strukul. G., "Transition Metal Catalysis in the Baeyer—Villiger Oxidation of Ketones," *Angew. Chem. Int. Ed.*, 1998, 37, 1198–1209.

Theil, F. et al., "Kinetic Resolution of Aliphatic, 1,2–Diols by a Lipase–Catalyzed Sequential Acetylation," *Tetra. Lett.*, 1993, 34(2), 305–306.

Wang, Y–F. et al., "Lipase–Catalyzed Irreversible Transesterifications Using Enol Esters as Acylating Reagents: Preparative Enantio– and Regioselective Syntheses of Alcohols, Glycerol Derivatives, Sugars, and Organometallics," *J. Am. Chem. Soc.*, 1998, 110, 7200–7205.

Moravcova, et al., "Pig liver esterase catalyzed hydrolysis of methyl 2,3–DI–0–acetyl–5–deoxyα– and β–d–arabinofuranosides," *Carbvohydrate Chemistry*, 1998, 17, 1191–2202.

Crooke, S.T. et al., "Pharmacokinetic Properties of Several Nlovel Oligonucleotide Analogs in mice", *J. Pharmacol. Exp. Therapeutics*, 1996, 277, 923–937.

Hamm, M. L. et al., "Incorporation of 2'–Deoxy–2'–mercaptocytidine into Oligonucleotides via Phosphoramadite Chemistry," *J. Org. Chem.*, 1997, 62, 3415–3420.

Kabanov, A. V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Lipidic Nucleic Acids", *Tetrahedron Letts.*, 1995, 36, 3651–3654.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Oligonucleotide Conjugates: Alteration of the Pharmacokinetic Properties of Antisense Agents", *Nucleosides and Nucleotides*, 1995, 14, 969–973.

Moravcová, J. et al., "Pig Liver Esterase Catalyzed Hydrolysis of Methyl 2,3–Di–O–Acetyl–5–Deoxy–α– and β–D–Arabinofuranosides," *J. Carbohydrate Chem.*, 1998, 17(8), 1191–1202.

Wu, W.Y. et al., "Synthesis of Ardisinol II," *Synthesis*, 1998, 1619–1622.

Martin, P., "Ein neuer Zugang zu 2'–O–Alkylribonucleosiden und Eigenschaften deren Oligonucleotide", *Helvetica Chemica Acta*, 1995, 78, 486–504 (English abstract included).

Mishra, R.K. et al., "Improved leishmanicidal effect of phosphorotioate antisense oligonucleotides by LDL–medicated delivery", *Biochim. Et Biophysica*, 1995, 1264, 229–237.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Polushin, N. N. et al., "Synthesis of Oligonucleotides Containing 2'–Azido–and 2'–Amino–2'–deoxyuridine Using Phosphotriester Chemistry," *Tetra. Letts.*, 1996, 37(19), 3227–3230.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Shea, R.G. et al., "Synthesis, hybridization properties and antiviral activity of lipid–oligodeoxynucletide conjugates", *Nucl. Acids Res.*, 1990, 18, 3777–3783.

Svinarchuk, F.P. et al., "Inhibition of HIV proliferation in MT–4 cells by antisense oligonucleotide conjugated to lipophilic groups", *Biochimie*, 1993, 79, 49–54.

Thomson, J. B. et al., "Synthesis and Properties of Diuridine Phosphate Analogues Containing Thio and Amino Modifications," *J. Org. Chem.*, 1996, 61, 6273–6281.

* cited by examiner

PROCESS FOR THE SYNTHESIS OF OLIGOMERIC COMPOUNDS

CROSS REFERENCE TO RELATED APPLICATIONS

This application is a divisional of application Ser. No. 09/349,659 filed Jul. 8, 1999 which is a continuation-in-part U.S. application Ser. No. 09/111,678 filed Jul. 8, 1998 now U.S. Pat. No 6,326,478.

FIELD OF THE INVENTION

This invention relates to methods for the preparation of oligomeric compounds having phosphite, phosphodiester, phosphorothioate, phosphorodithioate or other linkages, and to intermediates useful in their preparation.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science,* 1990, 250, 997–1000; and Wu, H., et. al., *Gene,* 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual,* Second Ed., J. Sambrook, et al., Eds., Cold Spring Harbor Laboratory Press, 1989; and *Current Protocols In Molecular Biology,* F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual,* supra. See also "DNA-protein interactions and The Polymerase Chain Reaction" in Vol. 2 of *Current Protocols In Molecular Biology,* supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron,* 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, has significant disadvantages. For example, cyanoethyl phosphoramidite monomers are quite expensive. Although considerable quantities of monomer go unreacted in a typical phosphoramidite coupling, unreacted monomer can be recovered, if at all, only with great difficulty.

Another disadvantage of using a β-eliminating cyanoethoxy group is formation of acrylonitrile upon removal of the phosphorus protecting group. Acrylonitrile is a highly toxic agent as well as a suspected carcinogen (See 1994–1995 Aldrich Chemical Company Catalog, at page 32). Acrylonitrile is also suspected of forming cyclic structures with thymidine resulting in oligomeric compounds having decreased hybridization ability. These modified oligomeric compounds are undesirable because they are difficult to separate from the desired oligomeric compound.

Consequently, there remains a need in the art for synthetic methods that will overcome these problems.

Several processes are known for the solid phase synthesis of oligonucleotide compounds. These are generally disclosed in the following U.S. Patents: U.S. Pat. No. 4,458,066; issued Jul. 3, 1984; U.S. Pat. No. 4,500,707, issued Feb. 19, 1985; and U.S. Pat. No. 5,132,418, issued Jul. 21, 1992. Additionally, a process for the preparation of oligonucleotides using phosphoramidite intermediates is disclosed in U.S. Pat. No. 4,973,679, issued Nov. 27, 1990.

A process for the preparation of phosphoramidites is disclosed in U.S. Pat. No. 4,415,732, issued Nov. 15, 1983.

Phosphoramidite nucleoside compounds are disclosed in U.S. Pat. No. 4,668,777, issued May 26, 1987.

A process for the preparation of oligonucleotides using a β-eliminating phosphorus protecting group is disclosed in U.S. Pat. No. Re. 34,069, issued Sep. 15, 1992.

A process for the preparation of oligonucleotides using a β-eliminating or allylic phosphorus protecting group is disclosed in U.S. Pat. No. 5,026,838, issued Jun. 25, 1991.

SUMMARY OF THE INVENTION

In one aspect of the present invention, methods are provided for the preparation of oligomeric compounds comprising a moiety having the Formula I:

wherein:
- A is a monocyclic or bicyclic aromatic ring system;
- $R^{11}$ and $R_{12}$ are each independently H, alkyl, aryl, heteroalkyl, heteroaryl, alkaryl, or aralkyl;
  - or $R_{11}$ and $R_{12}$ together with the carbon atoms to which they are attached form an optionally substituted aliphatic or aromatic ring having from 4 to 6 ring atoms;
- $X_4$ is alkaryl, aralkyl, sulfoxyl, sulfonyl, thio, substituted sulfoxyl, substituted sulfonyl, or substituted thio, wherein said substituent is alkyl, aryl, or alkaryl;
  - or $X_4$ is a group of formula $-C(=O)-(O)_{aa}-R_{40}$ where aa is 0 or 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups;
  - or $X_4$ is a group of formula $-(-CH_2-CH_2-)_d Si(R_9)_3$ where d is 0 or 1;
    - each $R_9$ is, independently, alkyl having 1 to about 10 carbon atoms, or aryl having 6 to about 10 carbon atoms;
- $X_1$ and $X_5$ are each independently O or S; comprising:
  (a) providing a compound having the Formula II:

wherein:

each $R_1$, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_1$ is a group of formula $Z-R_{22}-(R_{23})_v$;
  Z is O, S, NH, or $N-R_{22}-(R_{23})_v$;
  $R_{22}$ is $C_1$–$C_{20}$ alkyl, $C_2$–$C_{20}$ alkenyl, or $C_2$–$C_{20}$ alkynyl;
  $R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
  v is from 0 to about 10;

or $R_1$ has the formula:

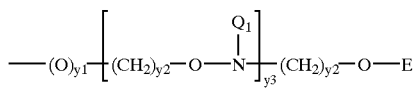

$y_1$ is 0 or 1;
$y_2$ is independently 0 to 10;
$y_3$ is 1 to 10;
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, substituted $C_1$–$C_{10}$ alkyl, dialkylaminoalkyl, a nitrogen protecting group, a tethered or untethered conjugate group, a linker to a solid support; or $Q_1$ and $Q_2$, together, are joined in a nitrogen protecting group or a ring structure that can include at least one additional heteroatom selected from N and O;
or $R_1$ has one of formula XI or XII:

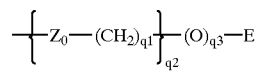

XI

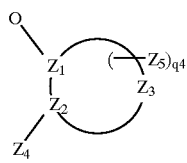

XII wherein
$Z_0$ is O, S, or NH;
$q^1$ is from 0 to 10;
$q^2$ is from 1 to 10;
$q^3$ is 0 or 1;
$q^4$ is, 0, 1 or 2;
$Z_4$ is $OM_1$, $SM_1$, or $N(M_1)_2$;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
$Z_1$, $Z_2$ and $Z_3$ comprise a ring system having from about 4 to about 7 carbon atoms, or having from about 3 to about 6 carbon atoms and 1 or 2 hetero atoms wherein said hetero atoms are selected from oxygen, nitrogen and sulfur, and wherein said ring system is aliphatic, unsaturated aliphatic, aromatic, or saturated or unsaturated heterocyclic; and
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;
$R_3$ is hydrogen, a hydroxyl protecting group, or a linker connected to a solid support;
each B, independently, is a naturally occurring or non-naturally occurring nucleobase or a protected naturally occurring or non-naturally occurring nucleobase;
n is 0 to about 50;
M is an optionally protected internucleoside linkage;
$R_5$ is —$N(R_6)_2$, or a heterocycloalkyl or heterocycloalkenyl ring containing from 4 to 7 atoms, and having up to 3 heteroatoms selected from nitrogen, sulfur, and oxygen; and $R_6$ is straight or branched chain alkyl having from 1 to 10 carbons; and
(b) reacting the compound of Formula II with a compound having Formula III:

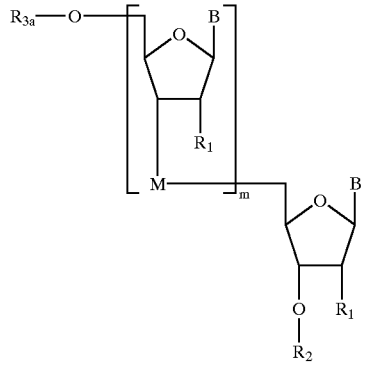

III wherein m is 0 to about 50;
$R_{3a}$ is hydrogen;
$R_2$ is hydrogen, a hydroxyl protecting group, or a linker connected to a solid support, provided that $R_2$ and $R_{3a}$ are not both simultaneously a linker connected to a solid support; to form the oligomeric compound.

Some preferred embodiments of the methods of the invention further comprise the step of oxidizing or sulfurizing the oligomeric compound. In some preferred embodiments, the methods of the invention further comprise transforming the oxidized or sulfurized oligomeric compound to form a further compound having the Formula III, where m is increased by 1. Other prefered embodiments further comprise a capping step, performed prior to or subsequent to oxidation or sulfurization.

In some preferred embodiments, the methods of the invention further comprising the step of cleaving the oligomeric compound from the solid support to produce a compound having the Formula IV:

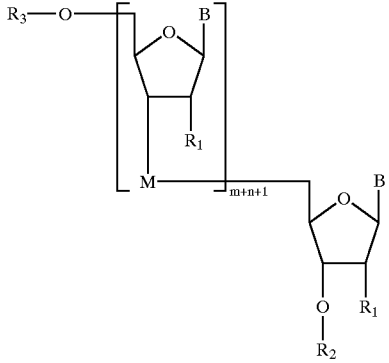

IV

In some preferred embodiments of the methods of the invention, A is phenyl or a naphthalene.

In further preferred embodiments of the methods of the invention, $X_4$ is benzoyl, acetyl (—C(=O)—$CH_3$) or levulinyl.

In some particularly preferred embodiments, $X_4$ is benzoyl, acetyl or levulinyl, A is phenyl, with the moiety —$OX_4$ being in the ortho or para position thereof, with the ortho position being more preferred.

In further preferred embodiments of the methods of the invention, $X_4$ is benzoyl, acetyl or levulinyl, A is a naphthalene ring connected to $X_5$ at the 1-position, with the moiety —$OX_4$ being in the 5- or 6-position of the naphthalene ring.

In further preferred embodiments of the invention, each $R_6$ is isopropyl.

In some especially preferred embodiments of the invention, n is 0. In further prefered embodiments, at least one of $X_1$ and $X_5$ is O. More preferably, $X_1$ and $X_5$ are each O.

In some especially preferred emboiments, n is 0; $X_4$ is benzoyl, acetyl or levulinyl; A is phenyl; —$OX_4$ is in the ortho or para position, with the ortho position being more preferred; $X_1$ and $X_5$ are each O; and $R_5$ is diisopropylamino.

In some preferred embodiments, the compound of Formula II is obtained by reaction of a compound having Formula V:

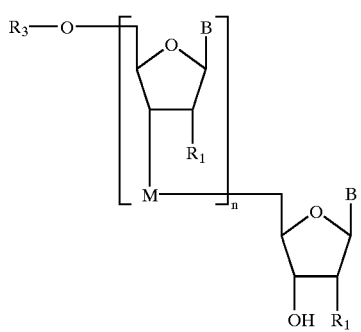

with a compound having the Formula VI:

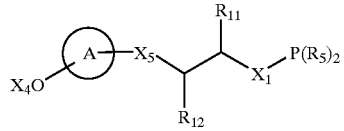

in the presence of an acid, preferably tetrazole. Preferably, $R_5$ is N,N-diisopropylamino.

In other preferred embodiments, the compound of Formula II is obtained by (a) reacting a compound having Formula-V with a chlorophosphine compund of formula $ClP(R_5)_2$ in the presence of a base; and (b) contacting the product of step (a) with a compound of Formula XX:

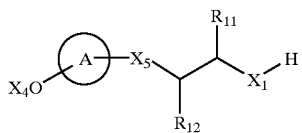

in the presence of an acid. Preferably, the chlorophosphine compound has the formula $ClP[(i-Pr)_2N]_2$.

Also provided in accordance with the present invention are compounds having Formula VII:

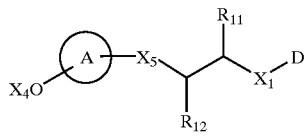

wherein:
A is a monocyclic or bicyclic aromatic ring system;
$R_{11}$ and $R_{12}$ are each independently H, alkyl, aryl, heteroaryl, alkaryl, or aralkyl;
or $R_{11}$ and $R_{12}$ together with the carbon atoms to which they are attached form an optionally substituted aliphatic or aromatic ring having from 4 to 6 ring atoms;
$X_4$ is alkaryl, aralkyl, sulfoxyl, sulfonyl, thio, substituted sulfoxyl, substituted sulfonyl, or substituted thio, wherein said substituent is alkyl, aryl, or alkaryl;
or $X_4$ is a group of formula —C(=O)—(O)$_{aa}$—$R_{40}$ where aa is 0 or 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups;
or $X_4$ is a group of formula —(—$CH_2$—$CH_2$—)$_d$Si$(R_9)_3$ where d is 0 or 1;
each $R_9$ is, independently, alkyl having 1 to about 10 carbon atoms, or aryl having 6 to about 10 carbon atoms;
$X_1$ and $X_5$ are each independently O or S;
D is $(R_7)(R_8)$P— or $(R_7)(R_8)$P(=$X_2$)—;
$R_8$ is $R_5$, or has the Formula VIII:

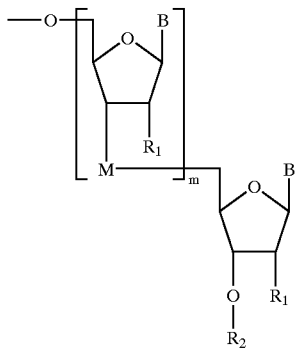

wherein:
each $R_1$, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
or $R_1$ is a group of formula Z—$R_{22}$—$(R_{23})_v$;
Z is O, S, NH, or N—$R_{22}$—$(R_{23})_v$;
$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

v is from 0 to about 10;

or $R_1$ has the formula:

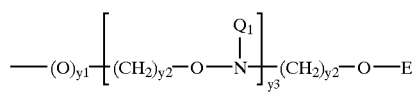

y1 is 0 or 1;
y2 is independently 0 to 10;
y3 is 1 to 10;
E is $C_1$–$C_{10}$ alkyl, $N(Q_1)(Q_2)$ or $N=C(Q_1)(Q_2)$;
  each $Q_1$ and $Q_2$ is, independently, H, $C_1$–$C_{10}$ alkyl, substituted $C_1$–$C_{10}$ alkyl, dialkylaminoalkyl, a nitrogen protecting group, a tethered or untethered conjugate group, a linker to a solid support; or $Q_1$ and $Q_2$, together, are joined in a nitrogen protecting group or a ring structure that can include at least one additional heteroatom selected from N and O;

or $R_1$ has one of formula XI or XII:

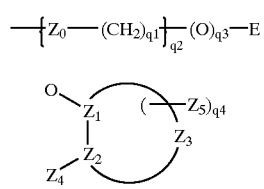

wherein
$Z^0$ is O, S, or NH;
$q^1$ is from 0 to 10;
$q^2$ is from 1 to 10;
$q^3$ is 0 or 1;
$q^4$ is, 0, 1 or 2;
$Z_4$ is $OM_1$, $SM_1$, or $N(M_1)_2$;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
$Z_1$, $Z_2$ and $Z_3$ comprise a ring system having from about 4 to about 7 carbon atoms, or having from about 3 to about 6 carbon atoms and 1 or 2 hetero atoms wherein said hetero atoms are selected from oxygen, nitrogen and sulfur, and wherein said ring system is aliphatic, unsaturated aliphatic, aromatic, or saturated or unsaturated heterocyclic; and
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;

each $X_2$ is O or S;
$R_5$ is $-N(R_6)_2$, or a heterocycloalkyl or heterocycloalkenyl ring containing from 4 to 7 atoms, and having up to 3 heteroatoms selected from nitrogen, sulfur, and oxygen;
M is an optionally protected internucleoside linkage;
m is 0 to about 50;
each B, independently, is a naturally occurring or non-naturally occurring nucleobase or a protected naturally occurring or non-naturally occurring nucleobase; and
$R_7$ is $R_5$, or has the Formula IX:

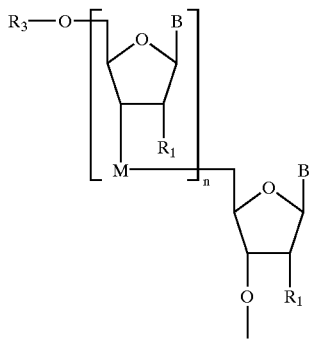

IX wherein:
$R_3$ is hydrogen, a hydroxyl protecting group, or a linker connected to a solid support;
n is 0 to about 50; with the proviso that the sum of m and n do not exceed 50.

In some preferred embodiments, $X_4$ is benzoyl, acetyl or levulinyl, with acetyl being preferred.

In some partiularly preferred embodiments, $X_4$ is benzoyl, acetyl or levulinyl, A is phenyl, with the moiety $-OX_4$ being in the ortho or para position, with the ortho position being more preferred, and $R_{11}$ and $R_{12}$ are each H.

In further preferred embodiments of the methods of the invention, $X_4$ is benzoyl, acetyl or levulinyl, A is a naphthalene ring connected to $X_5$ at the 1-position, with the moiety $-OX_4$ being at the 5- or 6-position of the naphthalene ring, and $R_{11}$ and $R_{12}$ are each H.

In some preferred embodiments, at least one of $X_1$ and $X_5$ is O. In more preferred embodiments, $X_1$ and $X_5$ are each O.

In particularly preferred embodiments, $X_4$ is benzoyl, acetyl or levulinyl, A is phenyl with $-OX_4$ being in the ortho or para position, $X_1$ and $X_5$ are each O, and $R_{11}$ and $R_{12}$ are each H.

In some preferred embodiments, $R_8$ is $R_5$. In further preferred embodiments, n is 0. In still further preferred embodiments, $R_8$ is $R_5$, n is 0, $X_4$ is benzoyl, acetyl or levulinyl, A is phenyl with $-OX_4$ attached at the ortho or para position; $X_1$ and $X_5$ are each O, and $R_{11}$ and $R_{12}$ are each H.

In some preferred embodiments, $R_8$ has the Formula VIII, and $R_7$ has the Formula IX. In further preferred embodiments, $R_8$ has the Formula VIII, and $R_7$ has the Formula IX, and n is 0. In still further preferred embodiments, $R_8$ has the Formula VIII, and $R_7$ has the Formula IX, and n is 0 and m is 0. In still further preferred embodiments, $R_8$ has the Formula VIII, and $R_7$ has the Formula IX, n is 0, $X_4$ is benzoyl, acetyl or levulinyl, A is phenyl with $-OX_4$ attached at the ortho or para position, $X_1$ and $X_5$ are each O, $R_5$ is diisopropylamino, and $R_{11}$ and $R_{12}$ are each H.

In some preferred embodiments, at least one of $X_1$ and $X_5$ is S. In further preferred embodiments, A is $(R_7)(R_8)P—$.

In some preferred embodiments, the present invention provides compounds comprising a moiety of Formula:

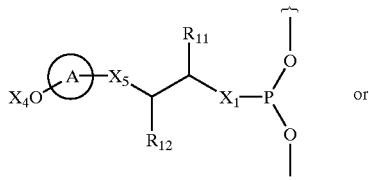

or

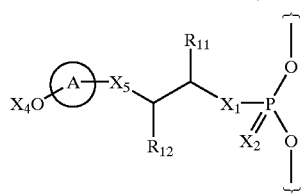

wherein the constituent variables are as previously defined.

Preferably, the moiety A is phenyl with $—OX_4$ attached at the ortho or para position, with the ortho position being preferred; or A is naphthalene connected to $X_5$ at the 1-position, and the moiety $—OX_4$ is attached to the 5- or 6-position of the naphthalene ring. In especially preferred embodiments, $X_4$ is benzoyl, acetyl or levulinyl, A is phenyl with $—OX_4$ is in the ortho or para position, and $X_1$ and $X_5$ are each O.

The present invention also provides compounds having Formula X:

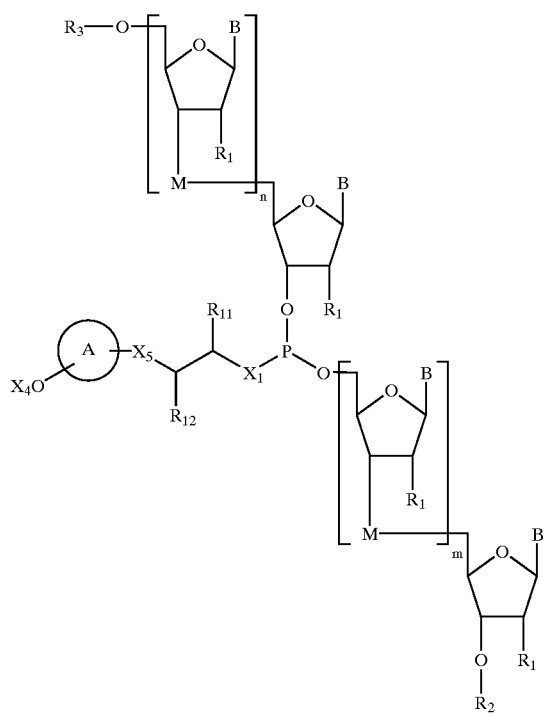

or Formula XI:

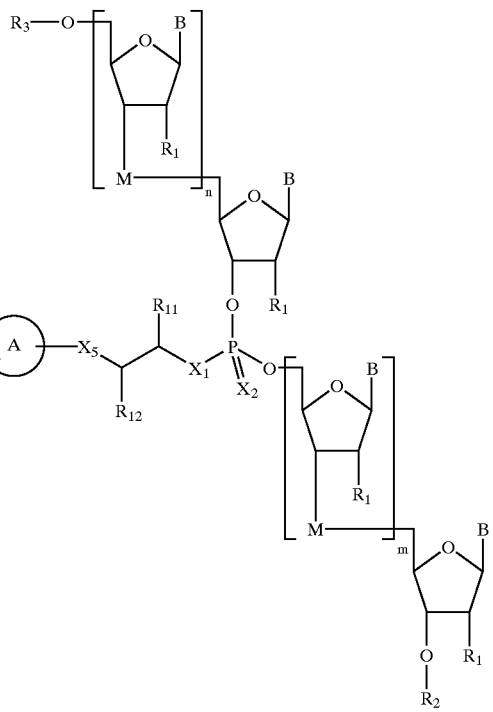

wherein m and n are each independently from 0 to about 50, provided that the sum of m and n does not exceed 50; and the other constituent variables are as previously defined.

In some preferred embodiments, $R_2$ is a linker connected to a solid support.

Also provided in accordance with the present invention are methods for the preparation of a compound of Formula II:

II

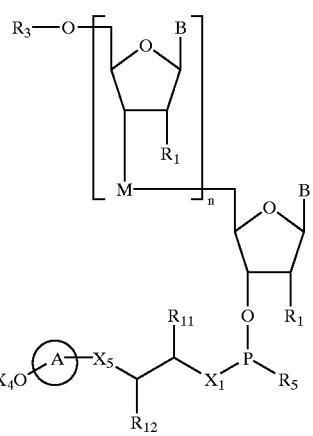

wherein the consitituent variables are as previously defined, comprising:

(a) selecting a 5'-protected nucleoside having Formula V:

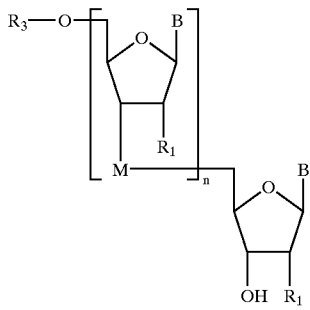

and (b) reacting the nucleoside with a compound having the Formula VI:

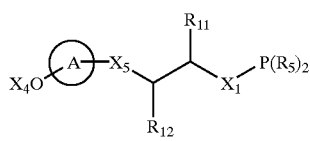

in the presence of an acid.

The present invention also provides methods for the preparation of a compound of Formula II comprising:

(a) selecting a 5'-protected nucleoside of Formula V:

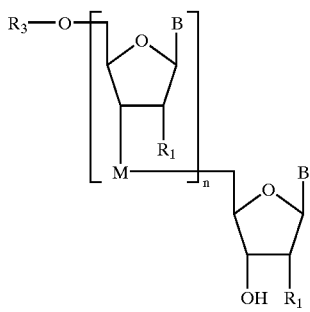

(b) reacting the protected nucleoside with a chlorophosphine compund of formula $ClP(R_5)_2$ in the presence of a base; and (c) contacting the product of step (b) with a compound of Formula XX:

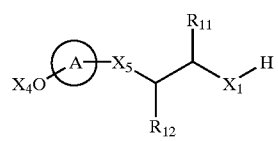

in the presence of an acid;

to form the nucleoside phosphoramidite.

In some preferred embodiments of the compounds of Formulas X and XI m and n are each 0.

Also provided in accordance with the present invention are compounds having the formula:

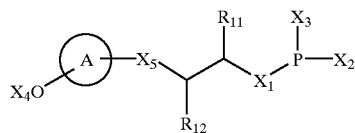

wherein A, $X_1$, $X_4$ $X_5$, $R_{11}$ and $R_{12}$ are as defined above, $X_2$ is halogen, and $X_3$ is —$N(R_6)_2$, or a heterocycloalkyl or heterocycloalkenyl ring containing from 4 to 7 atoms, and having up to 3 heteroatoms selected from nitrogen, sulfur, and oxygen. In further preferred embodiments, A is phenyl with —O—$X_4$ in the ortho or para position, $X_1$ and $X_5$ are O, and $R_{11}$ and $R_{12}$ are each H, and $X_4$ is benzoyl, acetyl or levulinyl. In still further preferred embodiments, $X_3$ is —$N(R_6)_2$ where $R_6$ is isopropyl. Preferably, $X_2$ is chlorine.

The present invention also provides products produced by the methods of the invention.

DESCRIPTION OF PREFERRED EMBODIMENTS

The present invention provides methods for the preparation of oligomeric compounds having phosphite, phosphodiester, phosphorothioate, or phosphorodithioate linkages, and to intermediates useful in their preparation.

In some preferred embodiments of the invention, methods are provided for the preparation of an oligomeric compound comprising at least one moiety having the Formula I:

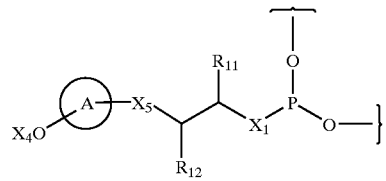

wherein:

A is a monocyclic or bicyclic aromatic ring system;

$R_{11}$ and $R_{12}$ are each independently H, alkyl, aryl, heteroaryl, alkaryl, or aralkyl;

or $R_{11}$ and $R_{12}$ together with the carbon atoms to which they are attached form an optionally substituted aliphatic or aromatic ring having from 4 to 6 ring atoms;

$X_4$ is alkaryl, aralkyl, sulfoxyl, sulfonyl, thio, substituted sulfoxyl, substituted sulfonyl, or substituted thio, wherein said substituent is alkyl, aryl, or alkaryl;

or $X_4$ is a group of formula —C(=O)—(O)$_{aa}$—$R_{40}$ where aa is 0 or 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups;

or $X_4$ is a group of formula —(—$CH_2$—$CH_2$—)$_d$Si $(R_9)_3$ where d is 0 or 1;

each $R_9$ is, independently, alkyl having 1 to about 10 carbon atoms, or aryl having 6 to about 10 carbon atoms;

$X_1$ and $X_5$ are each independently O or S; comprising:
(a) providing a compound having the Formula II:

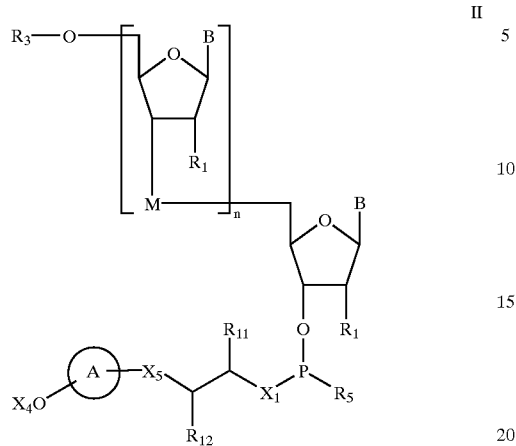

wherein:

each $R_1$, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_1$ is a group of formula Z—$R_{22}$—$(R_{23})_v$;

Z is O, S, NH, or N—$R_{22}$—$(R_{23})_v$;

$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, O-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmaco-dynamic properties of oligonucleotides, or a group that enhances the pharmacokinetic properties of oligonucleotides;

v is from 0 to about 10;

or $R_1$ has the formula:

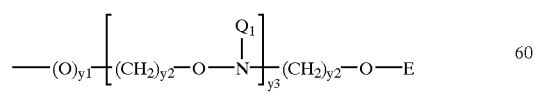

y1 is 0 or 1;
y2 is independently 0 to 10;
y3 is 1 to 10;
E is $C_1$–$C_{10}$ alkyl, $N(Q_1)(Q_2)$ or $N=C(Q_1)(Q_2)$;

each $Q_1$ and $Q_2$ is, independently, H, $C_1$–$C_{10}$ alkyl, substituted $C_1$–$C_{10}$ alkyl, dialkylaminoalkyl, a nitrogen protecting group, a tethered or untethered conjugate group, a linker to a solid support; or $Q_1$ and $Q_2$, together, are joined in a nitrogen protecting group or a ring structure that can include at least one additional heteroatom selected from N and O;

or $R_1$ has one of formula XI or XIII:

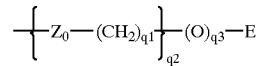

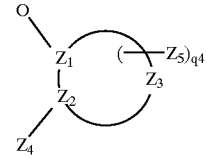

wherein $Z_0$ is O, S, or NH;
$q_1$ is from 0 to 10;
$q^2$ is from 1 to 10;
$q^3$ is 0 or 1;
$q^4$ is, 0, 1 or 2;
$Z_4$ is $OM_1$, $SM_1$, or $N(M_1)_2$;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
$Z_1$, $Z_2$ and $Z_3$ comprise a ring system having from about 4 to about 7 carbon atoms, or having from about 3 to about 6 carbon atoms and 1 or 2 hetero atoms wherein said hetero atoms are selected from oxygen, nitrogen and sulfur, and wherein said ring system is aliphatic, unsaturated aliphatic, aromatic, or saturated or unsaturated heterocyclic; and
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;

$R_3$ is hydrogen, a hydroxyl protecting group, or a linker connected to a solid support;

each B, independently, is a naturally occurring or non-naturally occurring nucleobase or a protected naturally occurring or non-naturally occurring nucleobase;

n is 0 to about 50;

M is an optionally protected internucleoside linkage;
$R_5$ is —$N(R_6)_2$, or a heterocycloalkyl or heterocycloalkenyl ring containing from 4 to 7 atoms, and having up to 3 heteroatoms selected from nitrogen, sulfur, and oxygen; and
$R_6$ is straight or branched chain alkyl having from 1 to 10 carbons; and (b) reacting the compound of Formula II with a compound having Formula III:

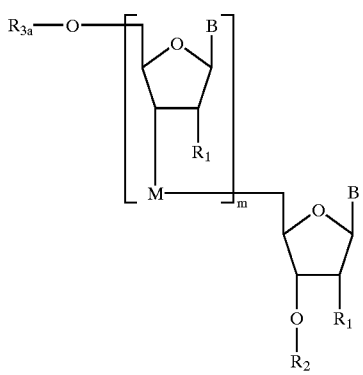

III wherein m is 0 to about 50;

$R_{3a}$ is hydrogen;

$R_2$ is hydrogen, a hydroxyl protecting group, or a linker connected to a solid support, provided that $R_2$ and $R_{3a}$ are not both simultaneously a linker connected to a solid support;

to form the oligomeric compound.

The methods of the present invention are useful for the preparation of oligomeric compounds containing monomeric subunits that are joined by a variety of linkages, including phosphite, phosphodiester, phosphorothioate, and/or phosphorodithioate linkages. As used herein, the term "oligomeric compound" is used to refer to compounds containing a plurality of nucleoside monomer subunits that are joined by internucleoside linkages, preferably phosphorus-containing linkages, such as phosphite, phosphodiester, phosphorothioate, and/or phosphorodithioate linkages. The term "oigomeric compound" therefore includes naturally occurring oligonucleotides, their analogs, and synthetic oligonucleotides. Monomer or higher order synthons having Formulas II or III above include both native (i.e., naturally occurring) and synthetic (e.g., modified native or totally synthetic) nucleosides and nucleotides.

In some preferred embodiments, a phosphoramidite protected at the 5'-position is reacted with the 3'-hydroxyl group of a compound of Formula III to produce phosphite compound containing the linkage of Formula I. Preferably, capping and/or oxidation or sulfurization steps are then performed to produce a compound of Formula IV.

Methods for coupling compounds of Formula II and Formula III of the invention include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the p$^v$ state using standard methods. This technique is commonly used for the synthesis of several types of linkages including phosphodiester, phosphorothicate, and phosphorodithioate linkages.

Typically, the first step in such a process is attachment of a first monomer or higher order subunit containing a protected 5'-hydroxyl to a solid support, usually through a linker, using standard methods and procedures known in the art. See for example, Oligonucleotides And Analogues A Practical Approach, Ekstein, F. Ed., IRL Press, N.Y., 1991, hereby incorporated by reference in its entirety. The support-bound monomer or higher order first synthon is then treated to remove the 5'-protecting group, to form a compound of Formula III wherein $R_2$ is a linker connected to a solid support. Typically, this is accomplished by treatment with acid. The solid support bound monomer is then reacted with a compound of Formula II to form a compound of Formula IV, which has a phosphite or thiophosphite linkage of Formula I. In preferred embodiments, synthons of Formula II and Formula III are reacted under anhydrous conditions in the presence of an activating agent such as, for example, 1H-tetrazole, 5-(4-nitrophenyl)-1H-tetrazole, or diisopropylamino tetrazolide.

In some preferred embodiments, phosphite or thiophosphite compounds containing a linkage of Formula I are oxidized or sulfurized as shown below to produce compounds having a linkage of Formula XII, where $X_1$ and $X_2$ can each be O or S:

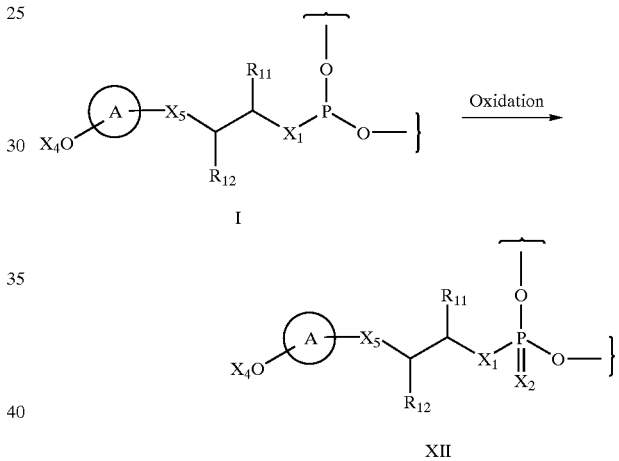

XII

Choice of oxidizing or sulfurizing agent will determine whether the linkage of Formula I will be oxidized or sulfurized to a phosphotriester, thiophosphotriester, or a dithiophosphotriester linkage.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Treatment with an acid removes the 5'-hydroxyl protecting group, and thus transforms the solid support bound oligomer into a further compound of Formula III wherein $R_{3a}$ is hydrogen, which can then participate in the next synthetic iteration; i.e., which can then be reacted with a further compound of Formula II. This process is repeated until an oligomer of desired length is produced.

The completed oligomer is then cleaved from the solid support. The cleavage step, which can precede or follow deprotection of protected functional groups, will in prefered embodiments yield a compound having Formula IV wherein $R_2$ is hydrogen. During cleavage, the linkages between monomeric subunits are converted from phosphotriester, thiophosphotriester, or dithiophosphotriester linkages to phosphodiester, phosphorothioate, or phosphorodithioate linkages.

Without intending that the invention be bound by any particular theory, it is believed that the loss of the oxygen or sulfur protecting group where $X_4$ is an alkanoyl (e.g., acetyl) group occurs via a fragmentation mechanism, illustrated in Scheme I below for embodiments wherein moiety A is phenyl with the group —$OX_4$ (exemplified as an acetyl group) in the para position:

Scheme I

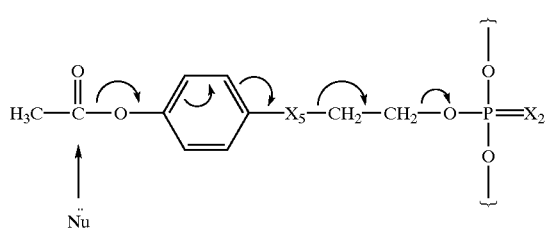

In this mechanism, a nucleophile (for example, ammonia) first attacks the carbonyl carbon of the acetoyl group. The resonant movement of electrons as depicted in Scheme I above is believed to cause the loss of the oxygen or sulfur protecting group via a fragmentation, thereby forming a phosphodiester, phosphorothioate, or phosphorodithioate linkage. The other products of the deprotection are Nu—C(=O)—$CH_3$, p-quinone, and ethylene gas.

The mechanism for embodiments wherein moiety A is phenyl with the group —$OX_4$ (exemplified as an acetyl group) attached to the ortho position is shown below in Scheme II:

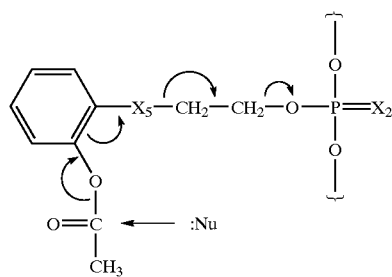

The products of the deprotection are the unprotected linkage, Nu-C(=O)—$CH_3$, o-quinone, and ethylene gas.

In some preferred embodiments of the compounds of the invention, substituent $X_4$ is selected such that it facilitates attack by a nucleophile, or a base. Accordingly, $X_4$ can be any of a variety of substituents, provided that it does not otherwise interfere with the methods of the invention. Preferred non-silyl $X_4$ groups include alkaryl groups, sulfoxyl groups, sulfonyl groups, thio groups, substituted sulfoxyl groups, substituted sulfonyl groups, or substituted thio groups, wherein the substituents are selected from the group consisting of alkyl, aryl, or alkaryl. More preferred non-silyl $X_4$ groups include compounds of formula —C(=O)—(O)$_{aa}$—$R_{40}$ where aa is 0 or 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups. Particularly preferred $X_4$ groups include acetyl (—C(=O)—$CH_3$), benzoyl (—C(=O)—Ph), phenylacetyl (—C(=O)—$CH_2$—Ph) and levulinyl (—C(=O)—$(CH_2)_2$—C(=O) —$CH_3$) groups.

In one embodiment of the invention the moiety —$OX_4$ forms a carbonate or substituted carbonate group. In some preferred embodiments, $X_4$ has the formula —C(=O)—(O)$_{aa}$—$R_{40}$ where aa is 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups. Carbonate protecting groups are discussed in for example, Green and Wuts, Protective Groups in Organic Synthesis, 2d edition, John Wiley & Sons, New York, 1991, pages 104–105 et al., incorporated herein by reference.

$X_4$ can also be a group of formula a group of formula —(—$CH_2$—$CH_2$—)$_d$Si($R_9$)$_3$ where d is 0 or 1, and each $R_9$ is, independently, alkyl having 1 to about 10 carbon atoms, or aryl having 6 to about 10 carbon atoms. While not wishing to be bound by a particular theory, it is believed that the loss of the oxygen or sulfur where $X_4$ is a trisubstituted silyl moiety, occurs via a fragmentation mechanism, illustrated in Scheme III below for embodiments wherein A is phenyl with —$OX_4$ at the para position:

Scheme III

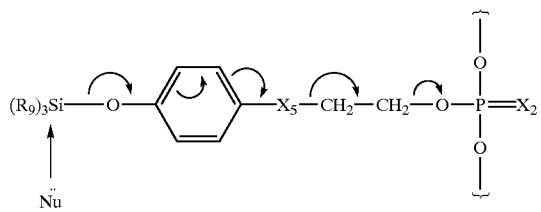

In this mechanism, a nucleophile attacks the silyl silicom atom, and the resonant movement of electrons as depicted in Scheme III above is believed to cause the loss of the oxygen or sulfur protecting group via a fragmentation mechanism, thereby forming a phosphodiester, phosphorothioate, or phosphorodithioate linkage. The other products of the deprotection are believed to be ethylene gas, p-quinone, and a compound of formula Nu—Si($R_9$)$_3$. For embodiments wherein the moiety ($R_9$)$_3$Si— is in the ortho position of the phenyl ring, the analogous fragmentation is beleived to result in the same products, except for the production of o-quinone instead of p-quinone. For embodiments wherein d is 1, it is believed that a similar fragmentation mechanism would produce the same products, and one additional mole of ethylene.

A wide variety of bases or nucleophiles can be used to initiate the fragmentation of the oxygen or sulfur protecting groups described herein. These include ammonium hydroxide, fluoride ion, alkyl amines, aqueous bases, and alkyl amines in combination with ammonium hydroxide. The resulting products include phosphate, phosphorothioate, and phosphorodithioate containing compounds.

Contact with fluoride ion preferably is effected in a solvent such as tetrahydrofuran, acetonitrile, dimethoxyethane, or water. Fluoride ion preferably is provided in the form of one or more salts selected from tetraalkylammonium fluorides (e.g., tetrabutylammonium fluoride (TBAF)), potassium fluoride, or cesium fluoride.

Preferably, conditions for removal of the oxygen or sulfur protecting group via fragmentation mechanisms described above also effect cleavage of the oligomeric compound from the solid support.

The methods of the present invention are useful for the preparation of oligomeric compounds from monomeric or oligomeric amidite synthons, for example synthons having Formula II. The internucleoside linkages of such oligomeric amidite synthons, represented by moiety M in the compounds and methods described herein, can be any internucleoside linkage as is known in the art, including phosphorus based linking groups such as phosphite, phosphodiester, phosphorothioate, and phosphorodithioate linkages, and other linkages known in the art. Such linkages can be protected, i.e., they can bear, for example, phosphate protecting groups. Included with the definition of internucleoside linkages are groups described herein, having the Formula:

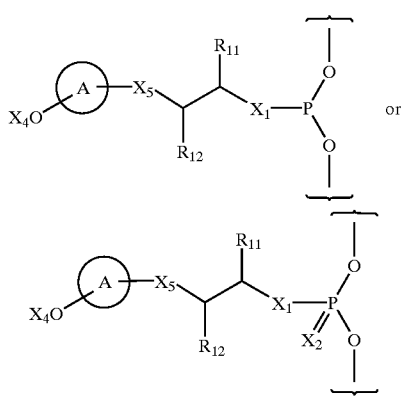

In preferred embodiments, the methods of the invention are used for the preparation of oligomeric compounds including oligonucleotides and their analogs. As used herein, the term "oligonuclotide analog" means compounds that can contain both naturally occurring (i.e. "natural") and non-naturally occurring ("synthetic") moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

Representative nucleobases useful in the compounds and methods described herein include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in Antisense Research and Application, Ed. S. T. Crooke and B. Lebleu, CRC Press, 1993, in Englisch et al., Angewandte Chemie, International Edition, 1991, 30, 613–722 (see especially pages 622 and 623, and in the Concise Encyclopedia of Polymer Science and Engineering, J. I. Kroschwitz Ed., John Wiley & Sons, 1990, pages 858–859, Cook, P. D., Anti-Cancer Drug Design, 1991, 6, 585–607, each of which are hereby incorporated by reference in their entirety. The term 'nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

As used herein the term "2'-substituent group" denotes groups attached to the 2' position of the ribosyl moiety, with or without an oxygen atom.

Preferred 2'-substituent groups described herein are represented in the compounds described herein by the variable $R_1$, which can be independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or $R_1$ is a group of formula $Z$—$R_{22}$—$(R_{23})_v$;

Z is O, S, NH, or N—$R_{22}$—$(R_{23})_v$;

$R_{22}$ is $C_1$–$C_{20}$ alkyl, $C_2$–$C_{20}$ alkenyl, or $C_2$–$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

v is from 0 to about 10;

or $R_1$ has the formula:

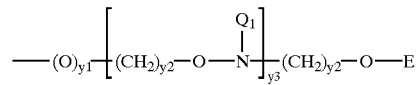

y1 is 0 or 1;
y2 is independently 0 to 10;
y3 is 1 to 10;
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a solid support; or $Q_1$ and $Q_2$, together, are joined in a nitrogen protecting group or a ring structure that can include at least one additional heteroatom selected from N and O;

or $R_1$ has one of formula XI or XII:

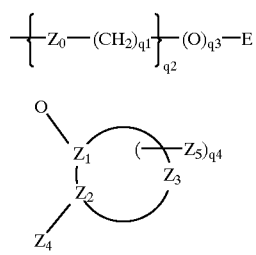

wherein
$Z_0$ is O, S, or NH;
$q_1$ is from 0 to 10;
$q^2$ is from 1 to 10;
$q^3$ is 0 or 1;
$q^4$ is, 0, 1 or 2;
$Z_4$ is $OM_1$, $SM_1$, or $N(M_1)_2$;
each $M_1$ is, independently, H, $C_1$–$C_8$ alkyl, $C_1$–$C_8$ haloalkyl, C (=NH)N(H)$M_2$, C(=O)N(H)$M_2$ or OC(=O)N(H)$M_2$;
$M_2$ is H or $C_1$–$C_8$ alkyl;
$Z_1$, $Z_2$ and $Z_3$ comprise a ring system having from about 4 to about 7 carbon atoms, or having from about 3 to about 6 carbon atoms and 1 or 2 hetero atoms wherein said hetero atoms are selected from oxygen, nitrogen and sulfur, and wherein said ring system is aliphatic, unsaturated aliphatic, aromatic, or saturated or unsaturated heterocyclic; and
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN.

Representative 2'—O—sugar substituents of formula XI are disclosed in U.S. patent application Ser. No.: 09/130,973, filed Aug. 7, 1998, entitled Capped 2'-Oxyethoxy Oligonucleotides, hereby incorporated by reference in its entirety.

Representative cyclic 2'—O—sugar substituents of formula XII are disclosed in U.S. patent application Ser. No.: 09/123,108, filed Jul. 27, 1998, entitled RNA Targeted 2'-Modified Oligonucleotides that are Conformationally Preorganized, hereby incorporated by reference in its entirety.

One particularly preferred group includes 2'-methoxyethoxy [2'—O—$CH_2CH_2OCH_3$, also known as 2'—O—(2-methoxyethyl) or 2'-MOE] (Martin et al., Helv. Chim. Acta, 1995, 78, 486), i.e., an alkoxyalkoxy group. A further referred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'—O—$CH_3$) and 2'-aminopropoxy (2'—$OCH_2CH_2CH_2NH_2$).

Further preferred 2'-sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$ where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., *Anti-Cancer Drug Design,* 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional 2' sugar modifications amenable to the present invention include 2'-SR and 2'-$NR_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.,* 1997, 62, 3415–3420. 2'-$NR_2$ nucleosides are disclosed by Goettingen, M., *J. Org. Chem.,* 1996, 61, 6273–6281; and Polushin et al., *Tetrahedron Lett.,* 1996, 37, 3227–3230.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, September 16–20, 1992, hereby incorporated by reference in its entirety. Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. As used herein, the term "lower alkyl" is intended to mean alkyl having 6 or fewer carbons.

As used herein, the term "ara_kyl" denotes alkyl groups which bear aryl groups, for example, benzyl groups. The term "alkaryl" denotes aryl groups which bear alkyl groups, for example, methylphenyl groups. As used herein the term "aryl" denotes aromatic cyclic groups including but not limited to phenyl, naphthyl, anthracyl, phenanthryl, and pyrenyl.

As used herein, the term "alkanoyl" has its accustomed meaning as a group of formula —C(=O)-alkyl. A preferred alkanoyl group is the acetyl group.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some embodiments of the invention, A is a monocyclic or bicyclic aromatic ring system. Suitable monocyclic or bicyclic aromatic ring systems include phenyl, naphthyl, pyridyl, furyl and indolyl.

In some preferred embodiments of the compounds and methods of the invention, $R_{11}$ and $R_{12}$ can be, together with the carbon atoms to which they are attached, an optionally substituted aliphatic or aromatic ring having from 4 to 6 ring atoms. Examples of such rings include phenyl and naphthyl. Examples of substituents for such rings include halogen, hydroxyl, alkyl, and acetyl groups. In more preferred embodiments, $R_{11}$ and $R_{12}$ are each H.

In some preferred embodiments of the invention $R_2$, or $R_3$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y., 1991, Chapter 1, pages 1–23.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., Tetrahedron Letters 1993, 34, 3373, hereby incorporated by reference in its entirety) and Poros—a copolymer of polystyrene/divinylbenzene.

In some preferred embodiments of the invention $R_2$, $R_3$ or $R_{3a}$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety.

Preferred protecting groups used for $R_2$, $R_3$ and $R_{3a}$ include dimethoxytrityl (DMT), monomethoxytrityl, 9-phenylxanthen-9-yl(Pixyl) and 9-(p-methoxyphenyl)xanthen-9-yl(Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or to other groups such as, for example, to 2'-alkoxy groups. Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, Protective Groups in *Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R. P., et.al., *J. Chem. Soc.,* 1990, 112, 1253–1254, and Iyer, R. P., et.al., *J. Org. Chem.,* 1990, 55, 4693–4699); tetraethylthiuram disulfide (see e.g., Vu, H., Hirschbein, B. L., *Tetrahedron Lett.,* 1991, 32, 3005–3008); dibenzoyl tetrasulfide (see e.g., Rao, M. V., et.al., *Tetrahedron Lett.,* 1992, 33, 4839–4842); di(phenylacetyl)disulfide (see e.g., Kamer, P. C. J., *Tetrahedron Lett.,* 1989, 30, 6757–6760); Bis(O,O-diisopropoxy phosphinothioyl)disulfids (see Stec et al., *Tetrahedron Lett.,* 1993, 34, 5317–5320); 3-ethoxy-1,2,4-dithiazoline-5-one (see *Nucleic Acids Research,* 1996 24, 1602–1607, and *Nucleic Acids Research,* 1996 24, 3643–3644); Bis(p-chlorobenzenesulfonyl)disulfide (see *Nucleic Acids Research,* 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/ water/pyridine or hydrogen peroxide/water or tert-butyl hydroperoxide or any peracid like m-chloroperbenzoic acid. In the case of sulfurization the reaction-is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferrred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, K., et al., *Chem. Pharm. Bull.*, 1987, 35, 833–836; Kumar, G., and Poonian, M. S., *J. Org. Chem.*, 1984, 49, 4905–4912; Bannwarth, W., *Helvetica Chimica Acta*, 1985, 68, 1907–1913; Wolter, A., et al., *nucleosides and nucleotides*, 1986, 5, 65–77, each of which are hereby incorporated by reference in their entirety.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

In some preferred embodiments of the methods of the invention, compounds of Formula II are prepared by reaction of a protected nucleoside having Formula V:

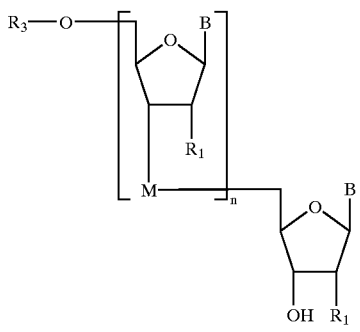

and a phosphine compound of Formula VI:

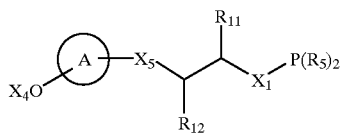

in the presence of an acid. Suitable acids include those known in the art to be useful for coupling of phosphoramidites, including, for example, tetrazole, substituted tetrazoles, dicyanoimidazole, or diisopropylammonium tetrazolide.

In some preferreed embodiments, compounds of Formula VI are prepared by reacting an alcohol having the Formula XX:

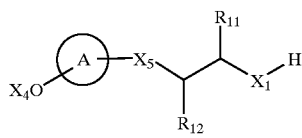

with phosphorus trichloride, and reacting the resultant product, $Cl_2P-X_1-(CH_2)_2-X_5-C_6H_4-OX_4$, with at least two equivalents of an amine having the formula $[(R_6)_2N]_2NH$. Each of the $R_6$ groups can be the same or different, and are preferably alkyl having 1 to about 10 carbon atoms, more preferably 1 to 6 carbon atoms, with 3 carbon atoms, and particularly isopropyl groups, being especially preferred.

In further preferred embodiments, compounds of Formula II can be prepared by reaction of a protected nucleoside of Formula V with a chlorophosphine compund of formula $ClP(R_5)_2$, where $R_5$ is preferably isopropylamino, followed by reaction with a compound of Formula XX in the presence of an acid, for example 1-H tetrazole, substituted tetrazoles, or dicyanoimidazole, with 1-H tetrazole being preferred.

In some particularly preferred embodiments of the foregoing methods, $X_4$ is benzoyl, acetyl or levulinyl, A is phenyl with the moiety $-OX_4$ being in the ortho or para position thereof, with the ortho position being more preferred, or A is naphthalene connected to $X_5$ at the 1-position, with the moiety $-OX_4$ being in the 5- or 6-position of the naphthalene ring.

In the compounds and methods of the present inventon, $X_1$ and $X_2$ can each independently be O or S. Thus, compounds having chiral phosphorus linkages are contemplated by the present invention. See Stec, W. J., and Lesnikowski, Z. J., in *Methods in Molecular Biology* Vol. 20: Protocols for Oligonucleotides and Analogs, S. Agrawal, Ed., Humana Press, Totowa, N.J. (1993), at Chapter 14. See also Stec, W. J. et al., *Nucleic Acids Research*, Vol. 19, No. 21, 5883–5888 (1991); and European Patent Application EP 0 506 242 A1, each of which are hereby incorporated by reference in their entirety.

Also provided in preferred embodiments of the invention are compounds having the general Formula VII:

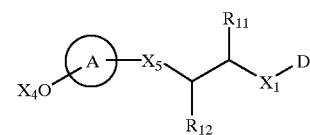

wherein $X_1$, A, $X_4$ and $X_5$ and D are as defined above.

In particularly preferred embodiments, the compounds of the invention have the Formula II:

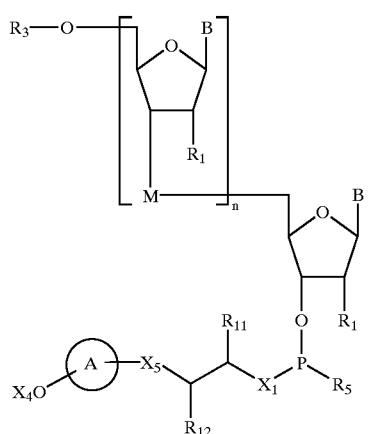

wherein:
$X_4$, M, $X_1$, $R_1$, $X_2$, $R_3$, B, n, and $R_5$ are defined as above.
In some especially preferred embodiments of the compounds of the invention having formula II above, $X_4$ is benzoyl, acetyl or levulinyl, or a group of formula $-(CH_2-CH_2)_d Si (R_9)_3$ where d is 0 or 1; A is phenyl having the moiety $-OX_4$ is in the ortho or para position, with the ortho position being preferred, $R_5$ is diisopropylamino, and n is 0.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLE

Example 1

2-Acetoxyphenoxyethyl Alcohol 2-(2-Hydroxyethoxy)phenol (308 g; 2 mol) was taken up in a 5 L Erlnmeyer flask fitted with mechanical stirrer. Anhydrous acetone (4 L, dried over $K_2CO_3$), and potassium carbonate powder (290 g; 2.1 mol) were added, and the mixture was stirred vigourously. Acetic anhydride (207 mL; 2.2 mol) was added from an additional funnel slowly over a period of 1 hour. Stiiring was continued for 3 hours. TLC ($CH_2Cl_2$/MeOH : 9:1, v/v) showed disapperence of starting material. The reaction mixture was filtered, solid washed thoroughly with acetone (1 L). The combined fractions was concentrated and purified by chromatography eluting with hexane and ethyl acetate (0% to 35% EtOAc; v/v). The product was obtained as a colorless viscous oil. Yield 258–264 gms (70–72%)

Example 2

General Method for the Synthesis of Phosphoramidites

A 500 mL two-necked flask equipped with a magnetic stirrer, a gas inlet for argon, and a septum was assembled under an argon atmosphere. All glassware were dried at 120° C. for 1 hour. The flask was charged with bis (diisopropylamino) chlorophosphine (84.6 mmol), Hünigs base (diisopropylethylamine) (105.8 mmol) and anhydrous dichloromethane (250 mL). With stirring, DMT-protected deoxyribonucleoside (70.5 mmol) was added as a solid over a period of 10 minutes. After 30 minutes, all the volatiles were removed under vacuum (oil pump) and the residue dissolved in anhydrous acetonitrile (150 mL). A solution of the 2-acetoxyphenoxyethyl alcohol (105.7 mmol) in acetonitrile (100 mL) was added followed by 1H-tetrazole (63 mmol). Stirring was continued for a further 1 hour. The reaction mixture was then concentrated, and the residue redissolved in dichloromethane (500 mL), washed with sodium bicarbonate solution and dried ($Na_2SO_4$). Concentration of the dried solution afforded the crude material which was purified by silica gel flash chromatography. The fractions corresponding to the amidites were combined and concentrated to afford the pure product as a foammy solid. Yields 65–80%.

Example 3

Preparation of 2-acetoxyphenoxyethyl N,N-diisopropyl phosphoramidite

A 500 mL three-necked flask equipped with a magnetic stirrer, a glass stopper and an inlet for argon was assembled under argon atmosphere. All glassware was dried in an oven at 120° C. for 1 hour. The reaction flask was charged with anhydrous ether (150 mL) and phosphorous trichloride (9.27 g; 67.5 mmol). 2-Acetoxyphenoxyethyl alcohol (50 mmol) in ether (100 mL) was added to the reaction flask slowly with stirring at 0° C. (ice cooling) using pressure-equalized addition funnel. After addition was complete, ice bath was removed and the reaction was stirred for three hours. The reaction mixture then was transferred to a 500 mL flask and concentrated under reduced pressure. To this product in anhydrous ether (200 mL) was added diisopropylamine (57.7 mL) at 0° C. under argon. After the addition was complete, stirring was continued at room temperature for 16 hours (overnight). The reaction mixture was filtered and concentrated to afford the product.

Example 4

General Method for the Synthesis of Phosphoramidites

A 250 mL two-necked flask equipped with a magnetic stirrer, a gas inlet for argon, and a septum was assembled under an argon atmosphere. All glassware was dried at 120° C. for 1 hour. The flask was charged with 5'-O-DMT nucleoside (7 mmol) and 1H-tetrazole (5.6 mmol). Anhydrous acetonitrile (50 mL) was added. To this stirred mixture under argon at room temperature was added a solution of 2-acetoxyphenoxyethyl N,N-diispropylphosphoramidite (10.5 mmol) in acetonitrile (50 mL). Usual workup followed by purification afforded the phosphoramidites.

Example 5

Synthesis of T—T Phosphorothioate Dimer 100 milligram (4 mmole) of 5'—O—Dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with dichloromethane and then with acetonitrile. Then, a 0.2 M solution of 5'-O-(4, 40-dimethoxytrityl)thymidine-3'-O-(2-acetoxyphenoxyethyl)-N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes. The aqueous solution was filtered, concentrated under reduced pressure to give phosphorothioate dimer of T—T.

Example 6

Synthesis of C–T Phosphorothioate Dimer 100 milligram (4 mmole) of 5'—O—Dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of $N^4$-Benzoyl-5'—O—(4,40-dimethoxytrityl)-2'-deoxycytidine-3'-O-(2-acetoxyphenoxyethyl)-N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes and then incubated at 55° C. for 12 hours. The aqueous solution was filtered, concentrated under reduced pressure and then treated at room temperature with 1.0 M solution of tetra-n-butyl ammonium fluoride in THF to give a phosphorothioate dimer of dC-T.

Example 7

Synthesis of 5'-TTTTTTT-3' Phosphorothioate Heptamer 50 milligram (2 mmole) of 5'—O—Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'—O—(4,4'-dimethoxytrityl)thymidine-3'—O—(2-acetoxyphenoxyethyl)-N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered, concentrated under reduced pressure to give a phosphorothioate heptamer of TTTTTTT.

Example 8

Synthesis of 5'-d(GACTT)-3' Phosphorothioate Tetramer 50 milligram (2 mmole) of 5'—O—Dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of 5'—O—(4,4'-dimethoxytrityl)thymidine-3'—O—(2-acetoxyphenoxyethyl)-N,N-diisopropylphosphoramidite) in acetonitrile and a 0.4 M solution of 1H-tetrazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A dichloromethane solution of 2% dichloroacetic acid (volume/volume) was added to deprotect the 5'-hydroxyl group. The product was washed with acetonitrile. Then, a 0.2 M solution of $N^4$-benzoyl-5'—O—(4,4'-dimethoxytrityl)-2'-deoxycytidine-3'—O—(2-acetoxyphenoxyethyl)-N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A dichloromethane solution of 2% dichloroacetic acid (volume/volume) was added to deprotect the 5'-hydroxyl group. The product was washed with acetonitrile. Then, a 0.2 M solution of $N^6$-benzoyl-5'—O—(4,4'-dimethoxytrityl)-2'-deoxyadenosine-3'—O—(2-acetoxyphenoxyethyl)-N,N-diisopropylphosphoramidite) in anhydrous acetonitrile and a 0.4 M solution of 1H-tetrazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product-was washed with acetonitrile.

A dichloromethane solution of 2% dichloroacetic acid (volume/volume) was added to deprotect the 5'-hydroxyl group. The product was washed with acetonitrile. Then, a 0.2 M solution of N²-isobutyryl-5'—O—(4,4'-dimethoxytrityl)-2'-deoxyguanosine-3'—O—(2-acetoxyphenoxyethyl)-N,N-diisopropylphosphoramidite) in acetonitrile and a 0.4 M solution of 1H-tetrazole in acetonitrile were added, and reacted at room temperature for 5 minutes. The product was washed with acetonitrile, and then a 0.05 M solution of Beaucage reagent in acetonitrile were added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes at room temperature and then incubated at 55° C. for 16 hours. The aqueous solution was filtered, and concentrated under reduced pressure to give a phosphorothioate tetramer of 5'-d (GACTT) -3'.

Example 9

Synthesis of Fully-modified 5'-d(TCC-CGC-CTG-TGA-CAT-GCA-TT)-3' Phosphorothioate 20-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile: for 2 minutes. At the end of synthesis, the support was washed with acetonitrile, cleaved, deprotected and purified in the usual manner.

Example 10

Synthesis of Fully-modified 5'-d(GCC-CAA-GCT-GGC-ATC-CGT-CA)-3' Phosphorothioate 20-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile: for 2 minutes. At the end of synthesis, the support was washed with acetonitrile, cleaved, deprotected and purified in the usual manner.

Example 11

Synthesis of Fully-modified 5'-d(GCG-TTT-GCT-CTT-CTT-CTT-GCG)-3' Phosphorothioate 21-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile: for 2 minutes. At the end of synthesis, the support was washed with acetonitrile, cleaved, deprotected and purified in the usual manner.

Example 12

Synthesis of Fully-modified 5'-d(GTT-CTC-GCT-GGT-GAG-TTT-CA)-3' Phosphorothioate 20-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 13

Synthesis of Fully-modified 5'-d(TCC-CGC-CTG-TGA-CAT-GCA-TT)-3' Phosphorothioate 20-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of phenylacetyl disulfide reagent in acetonitrile:picoline (1:1 v/v) for 2 minutes. At the end of synthesis, the support was washed with acetonitrile, cleaved, deprotected and purified in the usual manner.

Example 14

Synthesis of Fully-modified 5'-d(GCC-CAA-GCT-GGC-ATC-CGT-CA)-3' Phosphorothioate 20-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of phenylacetyl disulfide reagent in acetonitrile:picoline (1:1 v/v) for 2 minutes. At the end of synthesis, the support was washed with acetonitrile, cleaved, deprotected and purified in the usual manner.

Example 15

Synthesis of fully-Modified 5'-d(GCG-TTT-GCT-CTT-CTT-CTT-GCG)-3' Phosphorothioate 21-mer The synthesis of the above sequence was performed on a Pharmacia OligoPilot II Synthesizer on a 620 mmole scale using the 2-acetoxyphenoxyethyl phosphoramidites and Pharmacia's primar support. Detritylation was performed using 3% dichloroacetic acid in dichloromethane (volume/volume). Sulfurization was performed using a 0.2 M solution of phenylacetyl disulfide reagent in acetonitrile:picoline (1:1 v/v) for 2 minutes. At the end of synthesis, the support was washed with acetonitrile, cleaved, deprotected and purified in the usual manner.

Example 16

Acetylation of 2-(2-hydroxyethoxy)phenol

A 4 liter flask equipped with a mechanical stirrer, and an additional funnel is assembled under an atmosphere of argon. All the glassware is dried at 120° C. for 1 h. 2-(2-Hydroxyethoxyphenol) (508.8 g, 3.3 mole) was added to the flask as a solid and dissolved in anhydrous methylene chloride (2.2 L). Triethylamine (1.38 L, 9.9 mole) was added slowly followed by the addition of acetic anhydride (934 mL; 9.9 mole) at room temperature slowly over a period of 2 h. The reaction mixture becomes slightly warm. The reaction mixture was stirred at room temperature overnight. The reaction mixture was diluted with methylene chloride (1 L), washed with a solution of saturated sodium bicarbonate (till effervescence is complete), brine, dried over ($MgSO_4$) and concentrated. The crude material was distilled to afford 716 g (91%, b.p. 133–135° C./0.1 mm) of the title compound as a colorless viscous liquid.

Example 17

Chemoselective Hydrolysis using Bisacetate of 2-(2-hydroxyethoxy)phenol

A 1 liter flask equipped with a magnetic stirrer, a gas inlet for argon, and a septum was assembled under an atmosphere of argon. All the glassware was dried at 120° C. for 1 h. The bisacetate of 2-(2-hydroxyethoxyphenol) (35 g) was added to the flask and dissolved in anhydrous tetra-hydrofuran (350 mL). n-Butanol (52.5 mL) was added to the mixture followed by the addition of PLY Lipase (type II, Sigma). The reaction mixture was stirred at room temperature for 48 h (HPLC monitoring). The mixture was then filtered, the solid was washed with ethyl acetate (400 ml) and the combined fractions concentrated. Purification of the material by flash chromatography gave the 28 g of the title compound as a colorless viscous liquid.

Example 18

Hydrolysis of the Bisacetate of 2-(2-hydroxyethoxy)phenol using recycled enzyme

A 1 liter flask equipped with a magnetic stirrer, a gas inlet for argon, and a septum was assembled under an atmosphere of argon. All the glassware was dried at 120° C. for 1 h. The bisacetate of 2-(2-hydroxyethoxyphenol) (35 g) was added to the flask and dissolved in anhydrous tetrahydrofuran (350 mL). n-Butanol (52.5 mL) was added to the mixture followed by the addition of PPL Lipase (type II, Sigma). The reaction mixture was stirred at room temperature for 48 h (HPLC monitoring). The mixture was then filtered, the solid washed with ethyl acetate (600 mL) and the combined fractions concentrated. Purification of the material by flash column chromatography gave 26.8 g of the title compound as a colorless viscous liquid.

Example 19

Synthesis of 2Õ-(2-hydroxyethoxy)acetophenone

A 1 liter flask equipped with a magnetic stirrer, a gas inlet for argon, and a septum is assembled under an atmosphere of argon. All the glassware is dried at 120° C. for 1 h. 2 Õ-Hydroxyacetophenone (13.6 g) is added to the flask and dissolved in xylene (350 mL). Ethylene carbonate (17.6 g) is added to the mixture followed by the addtion of solid powdered potassium carbonate (55.2 g). The reaction mixture is stirred and refluxed for 12–15 h, cooled, filtered, and concentrated. Purification of the material by flash chromatography affords the title compound.

Example 20

Baeyer-Villiger oxidation of 2Õ-(2-hydroxyethoxy) acetophenone

A 250 mL flask equipped with a magnetic stirrer, a gas inlet for argon, and a septum is assembled under an atmosphere of argon. All the glassware is dried at 120° C. for 1 h. 2Õ-(2-Hydroxyethoxy)acetophenone (1.79 g, 10 mmol) is added to the flask and dissolved in anhydrous methylene chloride (25 mL). To this stirred solution at room temperature is added m-chloroperbenzoic acid (50–60% or any technical grade) as a solid. The reaction mixture is cooled to 5° C. and trifluoroacetic acid is added dropwise over a period of 5 min. The reaction mixture is protected from light and allowed to warm to room temperature. After 5 h, the reaction mixture is diluted with methylene chloride (25 ml), filtered, and the filtrate washed with a solution of saturated sodium carbonate, brine and dried. Concentration and purification using flash column chromatography affords the title compound.

Example 21

Synthesis of 4Õ-(2-hydroxyethoxy)acetophenone

A 1 L flask equipped with a magnetic stirrer, a gas inlet for argon, and a septum is assembled under an atmosphere of argon. All the glassware is dried at 120° C. for 1 h. 4 Õ-(2-Acetoxyethoxy)acetophenone (22.22 g) is added to the flask and dissolved in methanol (150 mL). Powdered potassium cyanide (13 g) is added to the solution and stirred at room temperature for 3 h. The reaction mixture is concentrated to a solid, taken up in minimum amount of methylene chloride and passed through a pad of silica gel. Concentration of the eluate affords the title compound.

Example 22

Baeyer-Villiger oxidation of 4Õ-(2-hydroxyethoxy) acetophenone

A 250 mL flask equipped with a magnetic stirrer, a gas inlet for argon, and a septum is assembled under an atmosphere of argon. All the glassware is dried at 120° C. for 1 h. 4Õ-(2-Hydroxyethoxy)acetophenone (1.79 g, 10 mmol) is added to the flask, dissolved in anhydrous methylene chloride (25 ml). To this stirred solution at room temperature is added m-chloroperbenzoic acid (50–60% or any technical grade) as a solid. The reaction mixture is cooled to 5° C. and trifluoroacetic acid is added dropwise over a period of 5 min. The reaction mixture is protected from light and allowed to warm to room temperature. After 5 h, the reaction mixture is diluted with methylene chloride (25 mL), filtered, and the filtrate washed with saturated sodium carbonate solution, brine and dried. Concentration and purification using flash chromatography affords the title compound.

Example 23

Synthesis of Fully Protected Diol

A 250 mL flask equipped with a magnetic stirrer, a gas inlet for argon, and a septum is assembled under an atmosphere of argon. All the glassware is dried at 120° C. for 1 h. 2-(2-Hydroxyethoxy)phenol (7.71 g) is added to the flask and dissolved in anhydrous methylene chloride (100 mL). Ethyl vinyl ether (3.97 g) is added to the solution followed by the addition of catalytic amount of PPTS. The reaction mixture is stirred at room temperature for 3 h. Triethylamine is added followed by the addition of acetic anhydride. The mixture is stirred at room temperature for 6 h, concentrated, taken up in ethyl acetate (150 mL), washed with a solution of sodium bicarbonate, brine, dried and concentrated. The crude title compound is used as such in the subsequent reaction.

Example 24

Hydrolysis of ethoxyethyl ether

A 250 mL flask equipped with a magnetic stirrer, a gas inlet for argon, and a septum is assembled under an atmosphere of argon. All the glassware is dried at 120° C. for 1 h. The fully protected 2-(2-hydroxyethoxy)phenol is taken up in methylene chloride and n-propanol is added to it followed by the addition of catalytic amount of pyridinium tosylate at 5° C. After stirring the mixture for 12 h, work up and purification by flash column chromatography affords the title compound.

Example 25

Synthesis of bis tert-butyldimethylsilyl ether of 2-(2-hydroxyethoxy)phenol A 250 mL flask equipped with a magnetic stirrer, a gas inlet for argon, and a septum is assembled under an atmosphere of argon. All the glassware is dried at 120° C. for 1 h. 2-(2-Hydroxyethoxy)phenol (7.71 g; 0.05 mole) is added to the flask and dissolved in anhydrous methylene chloride (100 mL). Triethylamine (20.2 g, 0.2 mole) is added to the solution followed by the addition of tert-butyldimethylsilyl chloride (18.09 g; 0.12 mole). A catalytic amount of DMAP is added to accelerate the reaction. The reaction mixture is stirred at room temperature for 12 h and then worked up and purified by flash column chromatography to give the title compound.

Example 26

Selective hydrolysis of bis tert-butyldimethylsilyl ether of 2-(2-hydroxyethoxy)phenol Bis tert-butyldimethylsilyl ether of 2-(2-hydroxy-ethoxy)phenol (0.01 mole) is taken up in methanol. Then 1 wt % (10 mg/mL) of solid iodine is added and the reaction monitored by tlc. Upon consumption of the alcoholic silyl ether, solid sodium metabisulfite is added and stirred until iodine color disappears. The methanolic solution is diluted with methylene chloride (120 mL), washed with saturated sodium bicarbonate, brine and dried. Purification by flash column chromatography affords the title compound.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the formula:

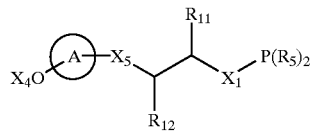

VI wherein

A is a diradical derived from a monocyclic or bicyclic aromatic ring system;

$R_{11}$ and $R_{12}$ are each H, independently alkyl, aryl, heteroalkyl, heteroaryl, alkaryl, or aralkyl;

or $R_{11}$ and $R_{12}$ together with the carbon atoms to which they are attached form an optionally substituted aliphatic or aromatic ring having from 4 to 6 ring atoms;

$X_4$ is alkaryl, aralkyl, sulfonyl, thiol, substituted sulfonyl, or substituted thiol, wherein said substituent is alkyl, aryl, or alkaryl;

or $X_4$ is a group of formula —C(=O)—(O)$_{aa}$—R$_{40}$ where aa is 0 or 1 and $R_{40}$ is lower alkyl, aryl, aralkyl, heteroaryl wherein said lower alkyl, aryl, aralkyl or heteroaryl groups are optionally substituted with one or more alkyl, aryl, aralkyl, halo or acetyl groups;

or $X_4$ is a group of formula —(—CH$_2$—CH$_2$—)$_d$Si(R$_9$)$_3$ where d is 0 or 1;

each $R_9$ is, independently, alkyl having 1 to about 10 carbon atoms, or aryl having 6 to about 10 carbon atoms;

$X_1$ and $X_5$ are each independently O or S;

$R_5$ is —N(R$_6$)$_2$, or a heterocycloalkyl or heterocycloalkenyl ring containing from 4 to 7 atoms, and having up to 3 heteroatoms selected from nitrogen, sulfur, and oxygen or optionally one of said $R_5$ groups is chloro; and $R_6$ is straight or branched chain alkyl having from 1 to 10 carbons.

2. The compound of claim 1 wherein A is phenylenyl with the moiety

—OX$_4$ in the ortho or para position, or A is naphthalidenyl connected to $X_5$ at the 1-position, with the moiety —OX$_4$ being in the 5- or 6-position, and $X_1$ and $X_5$ are each O.

3. The compound of claim 2 wherein $X_4$ is benzoyl, acetyl, or levulinyl.

4. The compound of claim 3 wherein one of said $R_5$ groups is —N(R$_6$)$_2$ where $R_6$ is isopropyl.

5. The compound of claim 4 wherein one of said $R_5$ groups is chloro.

* * * * *

UNITED STATES PATENT AND TRADEMARK OFFICE
CERTIFICATE OF CORRECTION

PATENT NO.    : 6,521,775 B2
DATED         : February 18, 2003
INVENTOR(S)   : Zacharia Cheruvallath et al.

It is certified that error appears in the above-identified patent and that said Letters Patent is hereby corrected as shown below:

Title page,
Item [56], References Cited, OTHER PUBLICATIONS,
"Sund" reference, please delete "Inramolecuolar" and insert therefor
-- Intermolecular --; "Stec" reference, (first occurrence) after "(deoxyribonucleoside phosphorothioates)" please insert -- Stereocontrolled synthesis of P-chiral oligo (deoxyribonucleoside phosphorothioates), --;
"Stec" reference, (second occurrence) please delete "Cos-Effective" and insert therefor -- Cost-Effective --;and please delete "Oligi" and insert therefor -- Oligo --; please delete "1,2,4-diathiazolidine" and insert therefor -- 1,2,4-dithiazolidine --;
"Basak" reference, please delete "βLactams:" and insert therefor -- β-Lactams: --; and "Xu" reference, please delete "Stereochemisry" and insert therefor
-- Stereochemistry --;
"Bisht" reference, please delete "Biotransfromations" and insert therefor
-- Biotransformations --;
"Chillemi" reference, please delete "Syntesis" and insert therefor -- Synthesis --; and please delete "Lysophophatidylnucleosides" and insert therefor
-- Lysophosphatidylnucleosides --; "Moravcova" reference, please delete "deoxya" and insert therefor -- deoxy-α --; and please insert -- J. -- before "Carbohydrate Chemistry,";
"Crooke" please delete "Nlovel" and insert therefor -- Novel --; and
"Hamm" reference, please delete "Phosphoramadite" and insert therefor
-- Phosphoramidite --;

Column 38,
Line 39, please delete "or optionally one of said R5 groups is chloro".

Signed and Sealed this

First Day of June, 2004

JON W. DUDAS
*Acting Director of the United States Patent and Trademark Office*